United States Patent [19]

Jiang

[11] Patent Number: 5,391,768

[45] Date of Patent: Feb. 21, 1995

[54] PURIFICATION OF 1,4-DIOXAN-2-ONE BY CRYSTALLIZATION

[75] Inventor: Ying Jiang, North Haven, Conn.

[73] Assignee: United States Surgical Corporation, Norwalk, Conn.

[21] Appl. No.: 36,922

[22] Filed: Mar. 25, 1993

[51] Int. Cl.⁶ .......................................... C07D 319/12
[52] U.S. Cl. .................................................. 549/274
[58] Field of Search ........................................ 549/274

[56] References Cited

U.S. PATENT DOCUMENTS

| | | | |
|---|---|---|---|
| 2,142,033 | 12/1938 | McNamee et al. | 549/274 |
| 2,163,109 | 6/1939 | Spanagel | 549/274 |
| 2,758,987 | 8/1956 | Salzberg | 549/274 |
| 2,840,548 | 6/1958 | Howk et al. | 549/274 |
| 2,900,395 | 8/1959 | Guest et al. | 549/274 |
| 3,020,289 | 2/1962 | Welpert | 549/274 |
| 3,063,967 | 11/1962 | Schultz | 549/274 |
| 3,063,968 | 11/1962 | Schultz | 549/274 |
| 3,119,840 | 1/1964 | Mayhew et al. | 549/274 |
| 3,190,858 | 6/1965 | Cox et al. | 549/274 |
| 3,280,065 | 10/1966 | Langner | 549/274 |
| 3,351,485 | 11/1967 | Langner | 549/274 |
| 3,391,126 | 7/1968 | Baggett et al. | 549/274 |
| 3,435,008 | 3/1969 | Schmitt et al. | 549/274 |
| 3,645,941 | 2/1972 | Snapp et al. | 549/274 |
| 3,952,016 | 4/1976 | Barillo et al. | 549/274 |
| 3,960,152 | 6/1976 | Augurt et al. | 549/274 |
| 4,033,938 | 7/1977 | Augurt et al. | 549/274 |
| 4,052,988 | 10/1977 | Doddi et al. | 549/274 |
| 4,070,375 | 1/1978 | Suzuki | 549/274 |
| 4,166,821 | 9/1979 | Suzuki | 549/274 |
| 4,643,191 | 2/1987 | Bezwada et al. | 549/274 |
| 4,646,741 | 3/1987 | Smith | 549/274 |
| 4,653,497 | 3/1987 | Bezwada et al. | 549/274 |
| 4,781,183 | 11/1988 | Casey et al. | 549/274 |
| 4,788,979 | 6/1988 | Jarrett et al. | 549/274 |
| 4,838,267 | 6/1989 | Jamiolkowski et al. | 549/274 |
| 4,966,982 | 10/1990 | Ono et al. | 549/274 |
| 4,994,551 | 2/1991 | Fung et al. | 549/274 |
| 5,007,923 | 4/1991 | Bezwada et al. | 549/274 |
| 5,023,350 | 6/1991 | Bhatia | 549/274 |
| 5,047,048 | 9/1991 | Bezwada et al. | 549/274 |
| 5,076,807 | 12/1991 | Bezwada et al. | 549/274 |
| 5,080,665 | 1/1992 | Jarrett et al. | 549/274 |
| 5,106,995 | 4/1992 | Plotkin | 549/274 |
| 5,142,054 | 8/1992 | Schaffner et al. | 549/274 |
| 5,179,216 | 1/1993 | Fobare et al. | 549/274 |

FOREIGN PATENT DOCUMENTS

| | | |
|---|---|---|
| 0411545 | 2/1991 | European Pat. Off. . |
| 0440448 | 8/1991 | European Pat. Off. . |
| 9101126 | 2/1991 | WIPO . |

OTHER PUBLICATIONS

Moore et al. Experimental Methods in Organic Chemistry, 2nd Ed. pp. 15–22 (1976).

Aethylenester der Glycol-und Oxalsäure und die Anhydride alpha-halogenisirter Fettsäuren', Berichte Der Deutschen Chemischen Gesellschaft, vol. 27, (1984), pp. 2939–2951, C. A. Bischoff et al.

Studien über äther-artige Verbindungen, VI. Mitteil. 1): Synthese der Äther-lactone vermittelst der Diäthersäuren', Berichte Der Deutschen Chemischen Gesellschaft, vol. 65 No. 6, (1932), M. H. Palomaa et al., pp. 924–925.

*Primary Examiner*—Joseph P. Brust

[57] ABSTRACT

Methods for purifying 1,4-dioxan-2-one includes dissolving a crude reaction product containing 1,4-dioxan-2-one in an aliphatic ester solvent, forming crystals of 1,4-dioxan-2-one, and filtering the mixture to recover solids containing crystalline 1,4-dioxan-2-one which is relatively pure compared to the crude reaction product.

14 Claims, No Drawings

PURIFICATION OF 1,4-DIOXAN-2-ONE BY CRYSTALLIZATION

PURIFICATION OF 1,4-DIOXAN-2-ONE BY CRYSTALLIZATION FIELD OF THE INVENTION

This invention relates generally to methods of purifying 1,4-dioxan-2-one. More particularly, this invention relates to the purification of 1,4-dioxan-2-one by recrystallization using a solvent comprising an aliphatic ester.

BACKGROUND OF THE INVENTION

Polymers made from 1,4-dioxan-4-one (also known as p-dioxanone) have been employed in the manufacture of absorbable surgical devices. See, for example, U.S. Pat. No. 4,052,988 to Doddi et al. The preparation of the p-dioxanone monomer is described by Doddi et al. as involving the reaction of ethylene glycol, metallic sodium and chloroacetic acid. After several steps including distillation, washing with acetone, addition of hydrochloric acid, precipitation with ethanol, filtration, heating and further distillation, Doddi et al. report that the purity of the crude dioxanone product is about 60–70 percent (See Example 1 of Doddi et al.). Doddi et al. further state that "exceptionally high purity of p-dioxanone monomer is required" to produce strong fibers of polydioxanone. However, although recognizing that high purity is required, Doddi et al. provide no details on how to achieve the required high purity, but rather merely state that the monomer is "finally purified to 99+% by multiple crystallizations and/or distillations" (See Doddi et al. column 4, lines 31–34).

More recent patents directed to polymers made at least impart from p-dioxanone include U.S. Pat. Nos. 4,643,191; 4,646,741; 4,653,497; 4,788,979; 4,838,267; 5,047,048; 5,007,923; 5,076,807; and 5,080,665. However, the steps necessary to achieve purification of the p-dioxanone monomer are not described in detail in these references.

U.S. Pat. No. 3,020,289 to Welpert describes the preparation of 2-p-dioxanone by passing vaporized diethylene glycol through a bed of copper chromite catalyst, with subsequent purification by fractional distillation. The p-dioxanone used in Example 1 of U.S. Pat. No. 3,063,967 to Schultz was twice distilled under nitrogen, presumably for purification. Other patents relating to the polymerization of p-dioxanone include U.S. Pat. No. 3,190,858; 3,391,126; and 3,645,941.

SUMMARY OF THE INVENTION

It has now been found that 1,4-dioxan-2-one can be purified by recrystallization from an aliphatic ester solvent. The method of the present invention includes the steps of: forming a solution by dissolving a crude reaction product containing 1,4-dioxan-2-one in an aliphatic ester; forming 1,4-dioxan-2-one crystals from the solution to form a mixture; and filtering the mixture to recover a solid containing 1,4-dioxan-2-one which is relatively pure compared to the crude reaction product. In particularly useful embodiments, the aliphatic ester is an alkyl acetate such as, for example, methyl or ethyl acetate. The step of forming the 1,4-dioxan-2-one crystals may include the steps of lowering the temperature of the solution and/or seeding the solution with 1,4-dioxan-2-one crystals.

The method of this invention allows for the recovery of very pure (99+%) dioxanone crystals in very good yield after only two recrystallizations.

DETAILED DESCRIPTION OF PREFERRED EMBODIMENTS

The methods of the present invention can be used to purify 1,4-dioxan-2-one which has been prepared by any method. For example, 1,4-dioxan-2-one can be prepared by the methods disclosed in U.S. Pat. Nos. 2,142,033; 2,900,395; 3,119,840; 4,070,375; and 4,166,821, the disclosures of which are incorporated herein by reference.

The resulting reaction product, including impurities which is to be purified by crystallization will hereinafter be referred to as the "crude reaction product". It should be understood, however that the reaction product may be subject to one or more processes such as, for example, distillation, washing or filtration prior to crystallization in accordance with the present invention. The term crude reaction product is intended to embrace reaction product which has been subject to such processes.

The 1,4-dioxan-2-one is purified from the crude reaction product by recrystallization using an aliphatic ester solvent. Suitable aliphatic esters are those of the formula:

$$RCOR'$$

where R is $C_1$–$C_4$ alkyl and R' is alkyl having 1–5 carbons. Particularly useful solvents include alkyl acetates (R=$CH_3$), such as methyl acetate (R'=$CH_3$) and ethyl acetate (R'=$C_2H_5$), with ethyl acetate being most preferred. Preferably, the solvent is a liquid at room temperature.

The crude reaction product is dissolved in the solvent to form a solution. The amount of reaction product dissolved in the solvent is preferably between about 400 and 700 grams per liter of solvent, depending on a number of factors including the reaction used to prepare the 1,4-dioxan-2-one, the specific reaction conditions employed and the composition of the resulting crude reaction product. Where diethylene glycol is used to prepare the 1,4-dioxan-2one, the amount of crude reaction product dissolved is typically from about 600 to about 900 grams per liter of solution.

The solution can be formed in any known way at temperatures ranging from below 0° C. to about 50° C., preferably with stirring. Once the solution is made, the next step is forming crystals of 1,4-dioxan-2-one.

The crystals of 1,4-dioxan-2-one can be formed using any crystallization technique. In a particularly useful embodiment of this invention, the solution is prepared at room temperature and crystallization is induced by lowering the temperature of the solution, preferably to below about −10° C. The lowered temperature is maintained a period sufficient to allow a desired amount of crystals to form. Normally, the lowered temperature is maintained for a period of time between about 30 minutes and 24 hours.

To provide for more rapid crystallization, the solution may be seeded, preferably with crystals of pure 1,4-dioxan-2-one. The seeding may be used together with any crystallization technique, or may, in itself, be used as the crystallization technique. From about 1 to about 10 grams of crystals are added per liter of solution.

Once crystallization has proceeded a desired amount, the resulting mixture is filtered to recover solids containing 1,4-dioxan-2-one which is relatively pure compared to the crude reaction product. The solids are then dried. Once dried, the solids may be further purified by repeating the above-described steps from one to ten or more additional times to achieve dioxanone of a desired purity.

EXAMPLE 1,4-dioxan-2-one is prepared by refluxing 1300 ml of diethylene glycol and 20 grams of copper chromite for six hours. The mixture is then distilled and 600 grams of crude product is obtained. Two hundred grams of the crude reaction product is dissolved in 200 ml of ethylacetate at room temperature to produce a yellowish solution. The mixture is then cooled to −20° C. After ten minutes, 2.0 grams of pure dioxanone crystals are added to the solution for seeding. After visual confirmation that crystals have formed (about 1 hour), the temperature of the solution is reduced to −34° C. for 2 hours. The mixture is then filtered and the filtrate is dried to provide about 100 grams of solids containing crystalline 1,4-dioxan-2-one. The solids are dissolved in 75 grams of ethyl acetate. The resulting solution is cooled to 0° C. and 1 gram of pure dioxanone crystals are added for seeding. The mixture is maintained at −30° C. for 12 hours and then filtered. Sixty to sixty-five grams of solids are obtained. NMR analysis shows the resulting product is 1,4-dioxan-2-one of excellent purity. This corresponds to about a 30% yield.

The purified dioxanone prepared in accordance with this invention can be used as a monomer to form polymers, such as homopolymers or copolymers (random, block graft). The polymers may be straight-chained, branched or star polymers. The copolymers may be made from dioxanone with any combination of other monomers known to form bioabsorbable materials. In addition, the polymers may be blended with other bioabsorbable polymers. The characteristics of the resulting polymer or blend can be tailored to desired specifications by controlling the composition, reaction conditions or blending parameters.

For example, the 1,4-dioxan-2-one prepared in accordance with Example 1 is polymerized by placing 5 grams of the 1,4-dioxan-2-one in a sialanized tube along with 0.5 ml of stannous octoate catalyst solution (0.2% stannous octoate in diethyl ether). The tube is evacuated slowly and held under vacuum for one hour at <1 Torr. The tube is then placed in a shaker oven and heated to 100° C. for 48 hours. The resulting polydioxanone has an intrinsic viscosity of 3.46 (average of measurements on three similarly produced samples) and is suitable for forming fibers.

The polymers formed from dioxanone monomers prepared in accordance with this invention can be formed into useful articles by molding, casting, pressing, grinding, extruding or spinning.

We claim:

1. A method for purifying 1,4-dioxan-2-one comprising:
   (a) forming a solution by dissolving a crude reaction product containing a compound of the formula

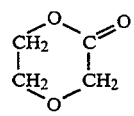

in an alkyl acetate;
   (b) forming crystals of said compound to form a mixture from the solution; and
   (c) filtering the mixture to recover solids containing said compound in crystalline form which is relatively pure compared to said crude reaction product.

2. A method as in claim 1, wherein said solution is formed at a first temperature, and said forming step comprising the step of lowering the temperature of said solution.

3. A method as in claim 1, wherein said forming step comprises the step of seeding said solution with 1-4-dioxan-2-one.

4. A method as in claim 2, wherein said first temperature is room temperature and the temperature of said solution is lowered to a temperature below about 0° C.

5. A method as in claim 1 further comprising the steps of:
   (d) forming a solution by dissolving solids containing crystalline 1,4-dioxan-2-one in an aliphatic ester; and
   (e) forming 1,4-dioxan-2-one crystals from the solution to form a mixture; and
   (f) filtering the mixture to recover solids containing crystalline 1,4-dioxan-2-one which is relatively pure compared to said crude reaction product.

6. A method as in claim 5, wherein said steps (d), (e) and (f) are repeated between 1 and 10 times.

7. A method as in claim 1, wherein the weight ratio of said crude reaction product to said alkyl acetate in said solution is between about 0.75:1.0 and 2:1.

8. A method as in claim 1, wherein said alkyl acetate is ethyl acetate.

9. A method as in claim 2, wherein the temperature of said solution is lowered to a temperature of about −10° C. or lower.

10. A method for purifying 1,4-dioxan-2-one comprising:
   (a) providing a crude reaction product containing a compound of the formula:

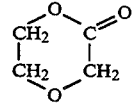

(b) dissolving said crude reaction product in an alkyl acetate at a first temperature to form a solution;
   (c) lowering the temperature of said solution;
   (d) seeding said solution by adding 1,4-dioxan-2-one thereto;
   (e) maintaining the seeded solution at a temperature below said first temperature for a period of time sufficient to allow crystallization of said compound thereby forming a mixture; and
   (f) filtering said mixture to recover solids containing said compound in crystalline form which is relatively pure compared to said crude reaction product.

11. A method as in claim 10, wherein said first temperature is room temperature and the seeded solution is maintained at a temperature below about 0° C. in said step (e).

12. A method as in claim 10, wherein said alkyl acetate is ethyl acetate.

13. A method as in claim 10, further comprising the steps of:
(g) forming a solution by dissolving the solids containing crystalline 1,4-dioxan-2-one from said step (f) in an aliphatic ester; and
(h) repeating said steps (c), (d), (e) and (f).

14. A method as in claim 10, wherein the weight ration of said crude reaction product to said alkyl acetate in said solution is between about 0.75:1 and 2:1.

* * * * *